(12) United States Patent
Herrmann et al.

(10) Patent No.: US 12,144,994 B2
(45) Date of Patent: Nov. 19, 2024

(54) HIS-BUNDLE PACING SYSTEM WITH LEFT-VENTRICULAR PACING

(71) Applicant: Cardiac Pacemakers, Inc., St. Paul, MN (US)

(72) Inventors: Keith L. Herrmann, Minneapolis, MN (US); Deepa Mahajan, North Oaks, MN (US); Stephen J. Hahn, Shoreview, MN (US); Allan Charles Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 894 days.

(21) Appl. No.: 16/238,275

(22) Filed: Jan. 2, 2019

(65) Prior Publication Data
US 2019/0201698 A1 Jul. 4, 2019

Related U.S. Application Data

(60) Provisional application No. 62/613,482, filed on Jan. 4, 2018.

(51) Int. Cl.
*A61N 1/37* (2006.01)
*A61N 1/365* (2006.01)
*A61N 1/368* (2006.01)

(52) U.S. Cl.
CPC ........... *A61N 1/3706* (2013.01); *A61N 1/365* (2013.01); *A61N 1/368* (2013.01); *A61N 1/3702* (2013.01);
(Continued)

(58) Field of Classification Search
CPC ....... A61N 1/371; A61N 1/3627; A61N 1/365
See application file for complete search history.

(56) References Cited

U.S. PATENT DOCUMENTS 6,212,434 B1 * 4/2001 Scheiner .............. A61N 1/0563
607/123
6,609,027 B2 8/2003 Kroll et al.
(Continued)

FOREIGN PATENT DOCUMENTS

WO WO-2019136073 A1 7/2019

OTHER PUBLICATIONS

Casavant, David Arthur, et al., "Systems and Methods for HIS-Bundle Pacing", U.S. Appl. No. 62/580,711, filed Nov. 2, 2017.
(Continued)

*Primary Examiner* — William J Levicky
(74) *Attorney, Agent, or Firm* — Schwegman Lundberg & Woessner, P.A.

(57) ABSTRACT

Systems and methods for cardiac pacing are described in this document. A medical system includes an electrostimulation circuit to generate His-bundle pacing (HBP) pulses to capture a His bundle, and LV pacing (LVP) pulses to capture a left ventricle. A sensing circuit may sense a cardiac activity, such as an atrial or an LV cardiac electrical activity. The system includes a control circuit controlling the delivery of HBP and LVP pulses. The HBP and LVP may be delivered concurrently or sequentially. In an example, the LVP pulses may be delivered based on a His-bundle capture status in response to the HBP pulse. The system may adjust one or more His-bundle stimulation parameters based on the His-bundle capture status.

20 Claims, 6 Drawing Sheets

(52) U.S. Cl.
CPC ............ *A61N 1/3704* (2013.01); *A61N 1/371* (2013.01); *A61N 1/3712* (2013.01)

(56) References Cited

U.S. PATENT DOCUMENTS

| | | | |
|---|---|---|---|
| 8,565,880 B2 | 10/2013 | Dong et al. | |
| 8,588,907 B2 | 11/2013 | Arcot-Krishnamurthy et al. | |
| 8,688,234 B2 | 4/2014 | Ortega et al. | |
| 8,761,880 B2 | 6/2014 | Maskara et al. | |
| 2002/0169484 A1* | 11/2002 | Mathis | A61N 1/368 607/9 |
| 2011/0264158 A1* | 10/2011 | Dong | A61B 5/7264 607/9 |
| 2011/0319956 A1* | 12/2011 | Zhu | A61N 1/3627 607/25 |
| 2013/0158621 A1* | 6/2013 | Ding | A61N 1/365 607/17 |
| 2014/0172035 A1* | 6/2014 | Shuros | A61N 1/36514 607/18 |
| 2019/0126049 A1* | 5/2019 | Casavant | A61N 1/056 |

OTHER PUBLICATIONS

"European Application Serial No. 19701403.8, Communication Pursuant to Article 94(3) EPC mailed Apr. 26, 2021", 6 pgs.

"European Application Serial No. 19701403.8, Response filed Feb. 15, 2021 to Communication pursuant to Rules 161(1) and 162 EPC mailed Aug. 13, 2020", 14 pgs.

"International Application Serial No. PCT/US2019/012059, International Preliminary Report on Patentability mailed Jul. 16, 2020", 8 pgs.

"International Application Serial No. PCT/US2019/012059, International Search Report mailed Mar. 14, 2019", 4 pgs.

"International Application Serial No. PCT/US2019/012059, Written Opinion mailed Mar. 14, 2019", 6 pgs.

* cited by examiner

HIS-BUNDLE PACING SYSTEM WITH LEFT-VENTRICULAR PACING

CLAIM OF PRIORITY

This application claims the benefit of priority under 35 U.S.C. § 119(e) of U.S. Provisional Patent Application Ser. No. 62/613,482, filed on Jan. 4, 2017, which is herein incorporated by reference in its entirety.

TECHNICAL FIELD

This document relates generally to medical systems, and more particularly, to systems, devices and methods for pacing of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium cause dyssynchronous contraction of the heart, resulting in poor hemodynamic performance, including a diminished blood supply to the heart and the rest of the body. For example, an abnormal delay in the transmission of the action potentials in the His bundle can cause irregular or dyssynchronous contractions of the ventricles, resulting in an abnormal rhythm of the heart.

Artificial cardiac pacing system have been used to rectify cardiac dyssynchrony and to improve hemodynamic performance. The artificial cardiac pacing system can deliver electrical stimulation to one or more portions of the heart such as to restore normal functioning of the heart to a certain extent. Right ventricular pacing directly excites the ventricular myocardium, rather than propagating the action potentials through the natural His-Purkinje conduction system. Long-term RV apex pacing may result in loss of synchronous contraction of RV and LV in some patients, partially due to delayed impulse propagation to the left ventricle, such as left bundle branch block. Consequently, permanent changes in myocardial perfusion and structure may develop over time in these patients, which may further result in a decrease in cardiac output and deterioration of ventricular function.

Bi-ventricular pacing involves both RV pacing via one lead and LV pacing via another lead, and has been demonstrated to help improve or restore synchronous contractions of both ventricles. However, BiV pacing also bypasses the His-Purkinje system. Additionally, although BiV pacing may restore ventricular synchrony to some extent in some patients, the intraventricular activations in RV or in LV is not as coordinated as with natural His-Purkinje activation.

Overview

Hemodynamic response to artificial pacing may depend on many factors, including pacing site and the manner of which the pacing is performed. Many patients receiving artificial pacing therapy have an intact His bundle and the natural His-Purkinje system, and therefore having normal ventricular activation. Conventional long-term RV apex pacing may cause a decrease in cardiac efficiency due to the uncoordinated contraction sequences, and eventually exhibit adverse long-term effects. Dyssynchronous contraction of the ventricles occurs during conventional RV pacing because the propagation of the activation sequence can be much slower when it occurs through working myocardium versus activation through the natural specialized conduction system of the heart. The cells of the specialized His-Purkinje system can propagate an activation signal about four times faster than working myocardium. A cardiac rhythm or functional management device configured to pace the His bundle is an alternative to conventional ventricular pacing. Pacing the His-bundle can activate the heart's natural conduction system, including the left and right bundle branches and Purkinje fibers, and produce efficient and coordinated cardiac response. This may reduce or eliminate the potential long-term harmful hemodynamic effects associated with continuous RV apical pacing.

However, the artificial cardiac pacing system targeting the natural specialized conduction system, when not being used effectively, may result in dyssynchronous ventricular contraction. For example, His-bundle pacing (HBP) may cause dyssynchronous patterns when electrostimulation fails to activate the His bundle, but only activates para-Hisian myocardium surrounding the His bundle, an undesirable event referred to as para-Hisian capture. In some cases, the HBP may activate both the His bundle and the adjacent working myocardium, an event referred to as non-selective His-bundle capture. There is an unmet need for an artificial cardiac pacing system to produce a desirable therapeutic effect of coordinated ventricular contraction via His bundle excitation, while reducing or eliminating unintended activation of non-targeted portions of the heart, such as the para-Hisian myocardium. Additionally, it is desired to retain the option of backup ventricular pacing if the HBP fails to produce propagating action potentials, such as due to inadequate stimulation energy, pacing lead failure, or a development of heart block inferior to the His bundle.

Biventricular (BiV) pacing involves electrostimulation of both left and right ventricles. Despite potential long-term harmful hemodynamic effect resulted from chronic RV pacing, LV pacing can be hemodynamically beneficial and remains a desirable therapy in many heart failure patients to restore cardiac synchrony and to improve cardiac performance. Some ambulatory medical devices (AMDs), such as implantable pacemakers or defibrillators, can deliver electrostimulation only to the left ventricle, known as LV-only pacing. Some AMDs can stimulate multiple sites of a heart chamber, such as multiple sites of a left ventricle. In contrast to a single site pacing (SSP), multisite pacing (MSP)

involves electrostimulation of two or more sites of a heart chamber simultaneously or sequentially within a cardiac cycle. Both SSP or MSP may improve cardiac performance in some patients.

Embodiments of the present subject matter provide systems, devices, and methods for cardiac pacing, including pacing the His bundle. The present inventors have recognized that an incorporation of LV pacing functionality, either SSP or MSP, into an artificial His-bundle pacing system may mitigate some undesirable hemodynamic outcome attributed to insufficient His-bundle capture. The LV pacing may serve as an option of backup ventricular pacing in case of no His-bundle capture. The LV pacing may also augment cardiac synchrony in case of His-bundle capture. For example, the LV pacing may improve the chance of activating certain slow-conducting fibers that interact with the natural His-Purkinje system, such as peripheral conduction fibers proximal to the His bundle, or conduction fibers extending from endocardium to epicardium layers.

One embodiment of the medical system discussed in this document includes an electrostimulation circuit that may generate His-bundle pacing (HBP) pulses to capture a His bundle, and LV pacing (LVP) pulses for delivering at or near the left ventricle. A sensing circuit may sense a cardiac activity, such as an atrial or an LV cardiac electrical activity. The system includes a control circuit controlling the delivery of HBP and LVP pulses. The HBP and LVP may be delivered concurrently, or sequentially such that the LVP pulses may be delivered after a programmable time delay subsequent to the delivery of the HBP pulses. In an example, the LVP pulses may be delivered based on a His-bundle capture status in response to the HBP pulse. The system may adjust one or more stimulation parameters based on the His-bundle capture status.

Example 1 is a system for pacing a heart. The system comprises an electrostimulation circuit configured to generate stimulation pulses for delivery at one or more target sites, and a control circuit. The system may optionally comprise a sensing circuit configured to sense cardiac activity. The control circuit can receive cardiac electrical activity, such as the sensed cardiac electrical activity from the sensing circuit. The control circuit includes a capture verification circuit configured to detect a His-bundle capture status using the received cardiac electrical activity, and a pacing control circuit configured to control the electrostimulation circuit to generate a His-bundle pacing (HBP) pulse to capture a His-bundle of the heart. The pacing control circuit may also control the electrostimulation circuit to generate a left-ventricular pacing (LVP) pulse to capture a left ventricle of the heart if the detected His-bundle capture status, in response to the delivery of the HBP pulse, satisfies a specific condition.

In Example 2, the subject matter of Example 1 optionally includes an ambulatory medical device (AMD) that includes a sensing circuit configured to sense cardiac activity, such as cardiac electrical activity. The AMD may optionally include the electrostimulation circuit or the control circuit. The AMD may be coupled to a first lead associated with one or more electrodes to deliver the HBP pulse, and coupled to a second lead associated with one or more left-ventricular electrodes to deliver the LVP pulse.

In Example 3, the subject matter of Example 2 optionally includes the sensing circuit that may be configured to electrically couple to one or more atrial electrodes associated with the second lead to sense an atrial activity. The pacing control circuit may be configured to control the electrostimulation circuit to generate and deliver the HBP pulse after a time interval subsequent to the sensed atrial activity.

In Example 4, the subject matter of any one or more of Examples 2-3 optionally includes the sensing circuit that may be electrically couple to the one or more electrodes associated with the first lead to sense a His-bundle activity of the heart.

In Example 5, the subject matter of any one or more of Examples 2-4 optionally includes the sensing circuit that may be coupled to the one or more left-ventricular electrodes associated with the second lead to sense left ventricular activity of the heart in response to the delivery of the HBP pulse. The capture verification circuit may be configured to detect the His-bundle capture status using the sensed left ventricular activity.

In Example 6, the subject matter of Example 5 optionally includes the capture verification circuit that may be configured to detect the His-bundle capture status using timing information of the sensed left ventricular activity.

In Example 7, the subject matter of Example 6 optionally includes the timing information of the sensed left ventricular activity that may include a paced His-to-left ventricular (Hp-LV) interval that represents a delay of the sensed left ventricular activity relative to the delivery of the HBP pulse. The capture verification circuit may be configured to detect the His-bundle capture status by comparing the Hp-LV interval to an intrinsic His-to-left ventricular (Hs-LV) interval measured during an intrinsic His-bundle activation.

In Example 8, the subject matter of Example 5 optionally includes the capture verification circuit that may be configured to detect the His-bundle capture status based on a morphology of the sensed left ventricular activity.

In Example 9, the subject matter of any one or more of Examples 1-8 optionally includes the capture verification circuit that may be configured to detect the His-bundle capture status, including to detect a presence or an absence of direct His-bundle depolarization resulted from the delivery of the HBP pulse. The electrostimulation circuit may be configured to generate the LVP pulse to capture the left ventricle in response to an absence of direct His-bundle depolarization.

In Example 10, the subject matter of Example 9 optionally includes the capture verification circuit that may be further configured to classify the detected His-bundle capture status as one of a selective capture, a non-selective capture, a para-Hisian capture, or a loss of capture. The electrostimulation circuit may be configured to generate the LVP pulse to capture the left ventricle if the detected His-bundle capture status is classified as a para-Hisian capture or a loss of capture.

In Example 11, the subject matter of Example 9 optionally includes the pacing control circuit that may be configured to adjust one or more HBP parameters in response to the detection of an absence of direct His-bundle depolarization. The electrostimulation circuit may be configured to generate an HBP pulse for delivery at the His-bundle to capture the His-bundle according to the adjusted one or more HBP parameters.

In Example 12, the subject matter of Example 11 optionally includes the electrostimulation circuit that may be configured to generate an HBP pulse to capture the His-bundle using an extended bipolar HBP vector in response to the detection of an absence of direct His-bundle depolarization. The extended bipolar HBP vector comprises a His-bundle electrode and a left-ventricular electrode.

In Example 13, the subject matter of Example 12 optionally includes the pacing control circuit that may be configured to determine the extended bipolar HBP vector, including to select the left-ventricular electrode, from two or more left-ventricular electrodes, based on a spatial proximity to a septum between ventricles of the heart.

In Example 14, the subject matter of any one or more of Examples 1-13 optionally includes the electrostimulation circuit that may be configured to deliver the HBP pulse and the LVP pulse concurrently.

In Example 15, the subject matter of any one or more of Examples 1-13 optionally includes the electrostimulation circuit that may be configured to deliver the LVP pulse after a specific time delay subsequent to the delivery of HBP pulse.

Example 16 is a system for pacing a heart. The system comprises an electrostimulation circuit configured to generate stimulation pulses for delivery at one or more target sites, and a control circuit. The system may comprise a sensing circuit configured to sense a cardiac activity. The control circuit may control the electrostimulation circuit to generate a His-bundle pacing (HBP) pulse to capture a His-bundle of the heart, and to generate a left-ventricular pacing (LVP) pulse to capture a left ventricle of the heart based on the received cardiac activity.

In Example 17, the subject matter of Example 16 optionally includes the electrostimulation circuit that may be configured to deliver the HBP pulse and the LVP pulse concurrently with, or after a specific time delay subsequent to, the delivery of HBP pulse.

Example 18 is a method for pacing a heart using an ambulatory medical device that is electrically coupled to at least a first lead associated with one or more His-bundle electrodes and a second lead associated with one or more left-ventricular electrodes and one or more atrial electrodes. The method comprises steps of: generating a His-bundle pacing (HBP) pulse using an electrostimulation circuit and delivering the HBP pulse to capture a His-bundle of the heart; sensing a cardiac activity, in response to the delivered HBP pulses, via a sensing circuit and one or more electrodes associated with the first or second lead; detecting a His-bundle capture status using the received cardiac activity; and generate a left-ventricular pacing (LVP) pulse using the electrostimulation circuit and delivering the LVP pulse to capture a left ventricular site of the heart if the detected His-bundle capture status satisfies a specific condition.

In Example 19, the subject matter of Example 18 optionally includes sensing the cardiac activity that may include sensing left ventricular activity of the heart in response to the delivery of the HBP pulse using at least one of the one or more left-ventricular electrodes associated with the second lead to sense, and detecting the His-bundle capture status includes using the sensed left ventricular activity.

In Example 20, the subject matter of Example 19 optionally includes sensing a paced His-to-left ventricular (Hp-LV) interval representing a delay of the sensed left ventricular activity relative to the delivery of the HBP pulse, and detecting the His-bundle capture status using a comparison of the Hp-LV interval to an intrinsic His-to-left ventricular (Hs-LV) interval measured during an intrinsic His-bundle activation.

In Example 21, the subject matter of Example 19 optionally includes detecting a presence or an absence of direct His-bundle depolarization resulted from the delivery of the HBP pulse, and generating the LVP pulse to capture the left ventricle in response to the detection of an absence of direct His-bundle depolarization.

In Example 22, the subject matter of Example 21 optionally includes adjusting one or more HBP parameters in response to the detection of an absence of direct His-bundle depolarization, and generating an HBP pulse to capture according to the adjusted one or more HBP parameters.

In Example 23, the subject matter of Example 22 optionally includes adjusting the one or more HBP parameters that may include switching to an extended bipolar HBP vector in response to the detection of an absence of direct His-bundle depolarization. The extended bipolar HBP vector comprises a His-bundle electrode and a left-ventricular electrode.

In Example 24, the subject matter of Example 18 optionally includes delivering the LVP pulse concurrently with, or after a specific time delay subsequent to, the delivery of HBP pulse.

The systems, devices, and methods discussed in this document may improve the technology of cardiac pacing in patients with cardiac disease, such as heart failure. A technological challenge in cardiac pacing is improving patient cardiac performance without structural and functional changes that impair cardiac synchrony, such as due to long-term RV apex pacing. Particularly, His-bundle pacing, although a promising technique to restore cardiac resynchronization in some patients, may have unintended consequences such as activation of non-targeted portions of the heart, such as the para-Hisian myocardium. The present subject matter provides a technical solution to this challenge by using combined HBP and LVP in a medical system or a device. The LVP may be used for backup ventricular pacing, or to augment His-bundle activation and to improve cardiac functionality. An embodiment of a system includes an ambulatory device coupled to a His-bundle lead and an LV lead. The LV lead includes multiple electrodes, including electrodes for atrial sense and pace, and electrodes for left ventricular sense and pace. The LV lead adds little additional cost or system complexity.

The HBP as discussed in the present document may improve pacing efficiency by utilizing the natural conduction system of the heart, while reducing long-term harmful hemodynamic effects associated with RV apex pacing. Additionally, integrated HBP and LVP therapy as discussed in this document may also help reduce unnecessary medical interventions, such as drugs, procedures, or device therapies. Reduced unnecessary device therapy may help save battery power and extend longevity of an implantable device. As a result, overall cost and power savings may be achieved in contrast to existing medical devices and systems.

While His-bundle pacing is specifically discussed in this document, this is meant only by way of example and not limitation. It is within the contemplation of the inventors, and within the scope of this document, that the systems, devices, and methods discussed herein may be applied to stimulate other conductive cardiac tissue, such as the right or left bundle branches or fascicles, or the Purkinje fibers.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for cardiac pacing. An embodiment of a medical system includes an electrostimulation circuit to generate His-bundle pacing (HBP) pulses to capture a His bundle, and to generate LV pacing (LVP) pulses for delivering at one or more sites of a left ventricle. A sensing circuit may sense a cardiac activity. The system includes a control circuit to control the delivery of HBP and LVP pulses. The HBP and LVP pulses may be delivered concurrently, or sequentially such that the LVP pulses may be delivered after a programmable time delay subsequent to the delivery of the HBP pulses. In an example, the LVP pulses may be delivered based on a His-bundle capture status in response to the HBP pulse. The system may adjust one or more stimulation parameters based on the His-bundle capture status.

Figure 1:
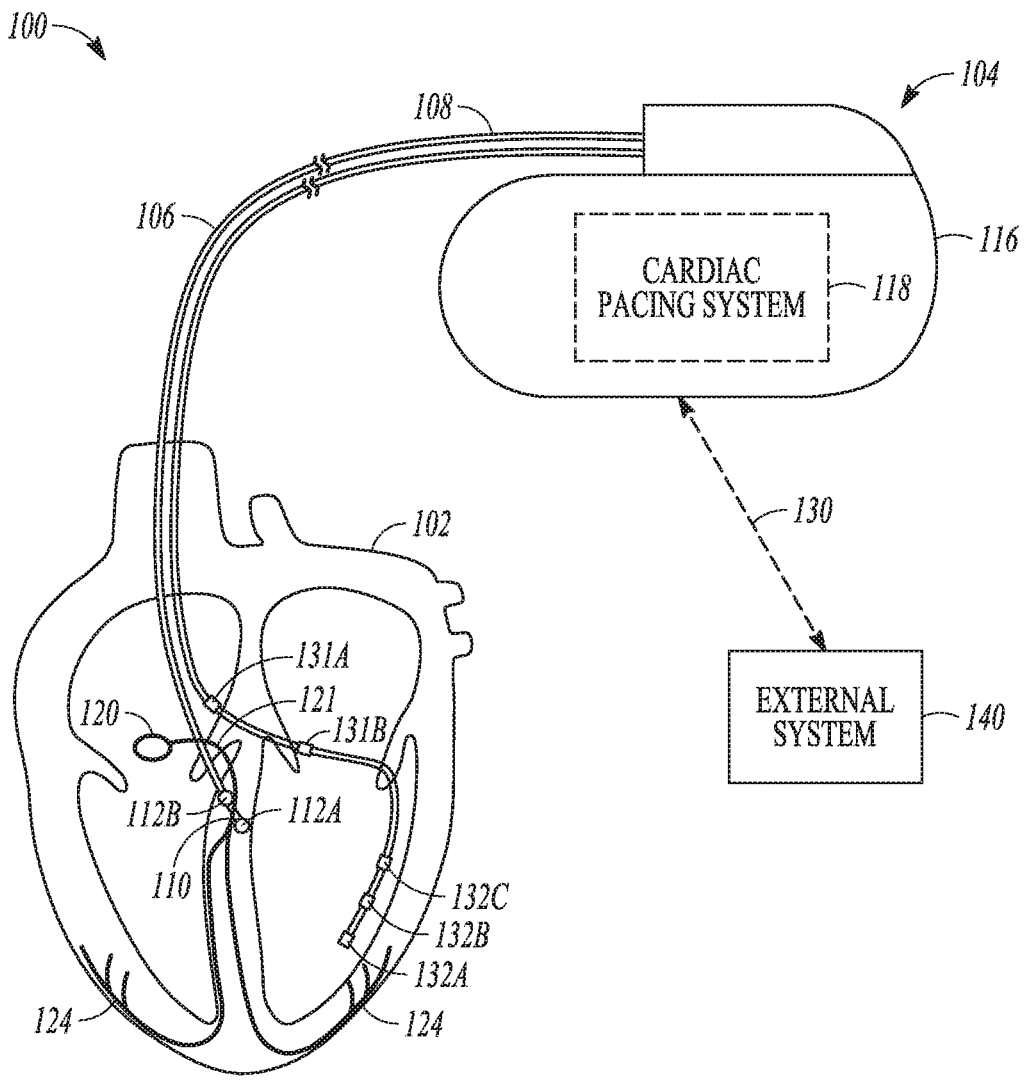
FIG. 1 illustrates generally an example of a cardiac disease management system and portions of an environment in which the system may operate.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include HBP. One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiologic signal indicative of cardiac activity, or a physiologic response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include at least a first lead 106 and a second lead 107. The lead 106 includes a proximal end 108 and a distal end 110. The proximal end 108 is configured to be connected to the IMD 104. The lead 106 includes one or more electrodes, such as located at the distal end 110, that are configured to deliver stimulation energy to the His bundle 121. FIG. 1 illustrates, by way of example and not limitation, two electrodes including a tip electrode 112A and a ring electrode 112B. The electrodes 112A-112B, among other electrodes that may be included in the lead 106, may be used to sense electrical activity and/or to deliver stimulation energy. The lead 106 may be placed such that one or more electrodes (e.g., 112A-112B), are positioned in or on a His bundle 121, a region distal to the blocked or slowly conducting AV node and in the AV septum, an interventricular septum region, or a right atrial (RA) region near the His-bundle 121. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissues, in addition to or in lieu of a region at or near the His bundle 121. In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102.

The lead 107 includes a proximal end that may be connected to the IMD 104 and a distal end that may be configured to be placed at a target location such as in a left ventricle (LV) of the heart 102. The lead 107 may be implanted through the coronary sinus, and placed in a coronary vein over the LV such as to allow for delivery of one or more LV pacing pulses. The lead 107 may include one or more distal electrodes such as electrodes 132A-132C, and one or more proximal electrodes such as electrodes 131A-131B. Each electrode may be electrically connected to the IMD 104 via a separate conductor in the lead 107. One or more of the distal electrodes 132A-132C may be used to deliver LVP pulses to the left ventricle, or to sense left ventricular activity, such as an LV electrogram (EGM). One or more of the proximal electrodes 131A-131B may be used to deliver pacing pulses to a supraventricular region (e.g., left atrium, right atrium, or a region close to the AV node or at the AV septum), or to sense supraventricular or atrial activity, such as atrial EGM. In some examples, one or more of the proximal electrodes 131A-131B may be used to deliver HBP pulses. For example, HBP pulses may be delivered using an extended bipolar pace vector consisting of one of the electrodes 112A-112B from the first lead 106 (e.g., as a cathode) and one of the proximal electrodes 131A-131B from the second lead 107 (e.g., as an anode). Compared to an AMD with multiple separate atrial and ventricular leads, a single lead 107 that includes one or more proximal electrodes (e.g., electrodes 131A-131B) and one or more distal electrodes (e.g., electrodes 132A-132C) may help reduce the system complexity, decrease implant time, simplify implant procedure, and reduce complications associated with multiple transvenously implanted leads. It may also improve the effectiveness of pacing therapy. Having the ability to pace the His bundle from different vectors (such as using electrodes associated with the single lead 107) may allow a physician to optimize pacing therapy. For example, in patients with conduction abnormalities (e.g., bundle branch block), it is desired to stimulate the His bundle from a location that is distal to the block and achieve activation of the blocked fibers. Having additional electrodes, such as those associated with the lead 107 in areas such as coronary sinus, may provide more options of pacing vectors using different combinations of those electrodes, thus allowing a clinician to optimize His bundle pacing and improve therapy outcome.

Although two leads 106 and 107 are shown in FIG. 1, this is meant to be illustrative rather than restrictive in nature or limiting in any way. In some examples, one or more other leads or catheters, such as an RV pace/sense lead and/or a defibrillation lead, may be included. Electrodes associated with the RV pace/sense lead and/or the defibrillation lead may be used to deliver HBP pulses, such as in conjunction with one of the electrodes 112A-112B from the first lead 106 to form an extended bipolar pace vector for delivering HBP pulses. In various examples, the cardiac disease management system 100 may include one or more stimulators or sensors untethered to a lead or catheter and in communication with the IMD 104 via a wireless link. Such leadless stimulators or sensors may deliver electrostimulation, sense a physiologic signal, such as cardiac electrical signals in response to cardiac stimulation, and transmit the sensed data to the IMD 104.

The IMD 104 may include a hermetically sealed housing 116 that houses a cardiac pacing system 118 and one or more other components including a communication circuit, a battery, a memory circuit, among others. The cardiac pacing system 118 includes an electrostimulation circuit configured to generate cardiac stimulation energy for delivery at one or more cardiac sites. In an example, the electrostimulation circuit may deliver HBP pulses at or near the His bundle 121, such as via the electrodes 112A or 112B associated with the lead 106. The electrostimulation circuit may additionally deliver LVP pulses at one or more left ventricular sites, such as via the distal electrodes 132A-132C associated with the lead 107.

The cardiac pacing system 118 may further include a sensing circuit to sense a physiologic signal using one or more electrodes associated with the lead system or a physiologic sensor. Examples of the physiologic signal may include an electrocardiogram (ECG), an intracardiac electrogram (EGM) such as an atrial EGM, a ventricular EGM, or a His bundle EGM, a thoracic impedance signal, a cardiac impedance signal, a pressure signal, among others. The cardiac pacing system 118 may sense the physiologic signal in response to the delivery of HBP pulses, and verify His-bundle capture status using the sensed physiologic signal. In an example, the sensed physiologic signal includes a far-field cardiac electrical signal representative of ventricular contractions, such as sensed via electrodes disposed at or near the His bundle or electrodes positioned in an atrium. To verify His-bundle capture status, the cardiac pacing system 118 may detect a His-bundle response representative of excitation of the His bundle directly resulting from the delivery of HBP pulses, and a detection of myocardial response representative of excitation of the para-Hisian myocardium directly resulting from the delivery of HBP pulses. The cardiac pacing system 118 may further classify capture status into one of a plurality of His-bundle capture types.

The cardiac pacing system 118 may control the delivery of LVP pulses based on the His-bundle capture status. In an example, LVP pulses may be delivered to the left ventricle if the HBP pulses fails to elicit capture of His-bundle tissue, or fails to elicit captures of both the His-bundle tissue and the para-Hisian myocardium (known as a loss of capture). The LVP pulses may be used as a backup therapy to improve myocardial contractility and to prevent ventricular a systole. The cardiac pacing system 118 may deliver LVP and HBP concurrently or sequentially with a specific time delay.

The cardiac pacing system 118 may adjust HBP delivery based on the His-bundle capture status to increase the chance of effective His bundle capture and avoid or reduce para-Hisian myocardium-only capture without direct His-bundle capture. The adjustment may include one or more HBP pacing parameters associated with amount of stimulation energy delivered to the His bundle. Additionally or alternatively, the adjustment may include electrode configurations for delivering the stimulation energy. For example, the cardiac pacing system 118 may switch to a different HBP pace vector if the His-bundle capture status indicates a loss of capture, or a myocardium-only capture without direct His-bundle capture.

The IMD 104 may be configured to communicate with an external system 140 via a communication link 130. The external system 140 may include a dedicated hardware/ software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiologic signals, analyzing the physiologic signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiologic signals collected from the patient 102, physiologic response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, or classify tissue response to one of a plurality of capture types. The capture verification or classification may be carried out periodically, or triggered by a specific event such as a user command. A user may use the external system 140 to program the IMD 104, such as to configure a pace vector (e.g., specifying anode and cathode electrodes) to deliver HBP, or to configure a sense vector to sense a physiologic signal.

The external system 140 may include a remote device in a location relatively distant from the IMD 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user (e.g., a clinician), or to a process (e.g., an instance of a computer program executable in a microprocessor). In an example, the process may include an automated generation of recommendations for initiating or titrating a medical therapy or an electrostimulation therapy. In an example, the external device 120 or the remote device 124 may include a respective display unit for displaying the physiologic signals, stimulation parameters, capture verification, or classification of capture types, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
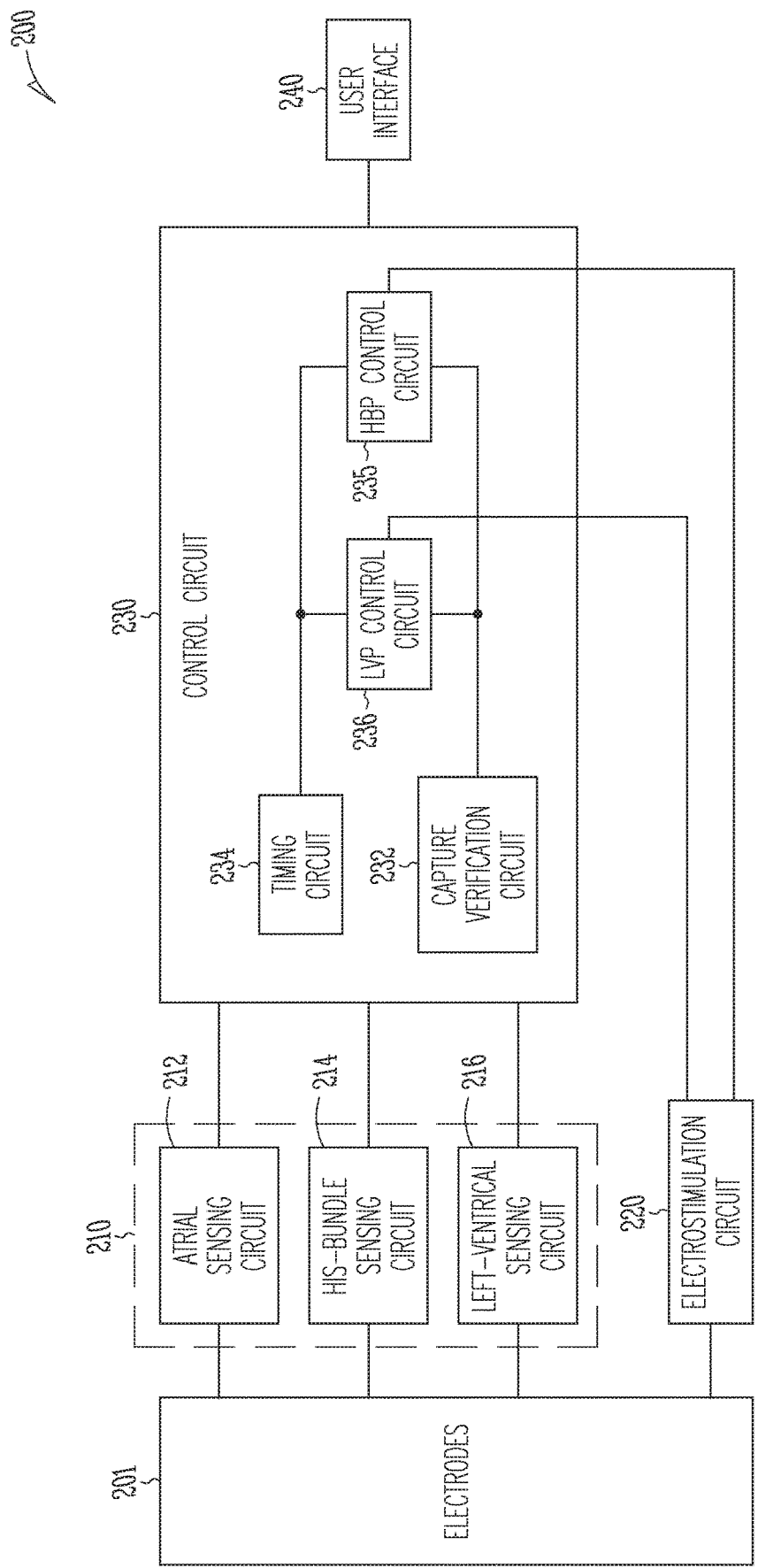
FIG. 2 is a block diagram illustrating an example of portions of a cardiac pacing system.

FIG. 2 is a block diagram illustrating an example of portions of a cardiac pacing system 200, which represents an embodiment of the cardiac pacing system 118. The cardiac pacing system 200 may include sensing circuitry 210, an electrostimulation circuit 220, a control circuit 230, and a user interface 240.

The sensing circuitry 210 may include sub-circuits each configured to sense one or more physiologic signals from a patient. Examples of the physiologic signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others. The sensed physiologic signals may include intrinsic cardiac activation signals (e.g., during an intrinsic sinus rhythm), or evoked cardiac activation signals (e.g., in response to cardiac stimulation) such as evoked response to His-bundle pacing.

As illustrated in FIG. 2, the sensing circuitry 210 may include one or more of an atrial sensing circuit 212, a His-bundle sensing circuit 214, and a left-ventricular sensing circuit 216. The atrial sensing circuit 212 may be coupled to one or more electrodes or physiologic sensors to sense an intrinsic atrial activation event (hereinafter referred to as an AS event), or to sense an evoked response to atrial pacing (hereinafter referred to as an AP event). In an example, the atrial sensing circuit 212 may be coupled to one or more of the proximal electrodes 131A-131B associated with the lead 107 to sense supraventricular cardiac electrical activity, such as an atrial EGM, and to detect AS or AP events from the sensed cardiac activity. The His-bundle sensing circuit 214 may be coupled to one or more electrodes or physiologic sensors to sense a His bundle activation event (HBS) in response to an intrinsic atrial activation, or in response to atrial pacing. The HBS event is subsequent to an AS event or an AP event within a cardiac. In an example, the His-bundle sensing circuit 214 may be coupled to one or more of the electrodes 112A-112B to sense an HBS event. The left-ventricular sensing circuit 216 may be coupled to one or more electrodes or physiologic sensors to sense cardiac activity from the left ventricle. In an example, the left-ventricular sensing circuit 216 may be coupled to one or more of the distal electrodes 132A-132C to sense LV activity such as LV EGM.

In various examples, one or more sub-circuits of the sensing circuitry 210 may be configured to sense a far-field cardiac electrical signal representing ventricular response to the delivery of the HBP pulses. In an example, the far-field cardiac electrical signal may be sensed using a unipolar sense vector comprising an electrode disposed at or near the His bundle (e.g., one of the electrodes 112A-112B) or in an atrium (e.g., one of the proximal electrodes 131A-131B), and a reference electrode distal to the His bundle, such as the housing 116 of the IMD 104. In another example, the far-field cardiac electrical signal may be sensed using a bipolar sense vector comprising two electrodes disposed at or near the His bundle or in an atrium. The electrode(s) for sensing the far-field cardiac electrical signal may be the same electrodes used for delivering HBP pulses. Alternatively, different electrodes may be used for sensing the far-field cardiac electrical signal. Far-field signals may provide a global perspective to the activation of the heart. For example, both atrial and ventricular activity may be present on an atrial EGM sensed by the atrial sensing circuit 212. The far-field cardiac electrical signal may be used by the control circuit 230 to verify His-bundle capture, or to classify a tissue response into one of a plurality of capture types.

The electrostimulation circuit 220 may be configured to generate stimulation energy for delivery at one or more cardiac sites via one or more electrodes 201. Stimulation energy (e.g., voltage or current) may be applied to a pace vector defined by a pair of electrodes including an anode and a cathode. The control circuit 230 may include sub-circuits configured to control the delivery of stimulation energy. The electrodes 201 may include tethered electrodes in association with one or more leads, catheters, or other stimulation delivery means. In an example, both anode and cathode of a pace vector may be associated with the same lead or catheter. In another example, the anode and cathode may be associated with different leads. The electrodes 201 may also include reference electrodes, such as the device housing 116 of the IMD 104, or an electrode associated with the device housing. In some examples, the electrodes 201 may include untethered electrodes, such as wireless pacing units, for actively delivering stimulation energy at respective target sites. The electrostimulation circuit 220 may be communicatively coupled to the untethered electrodes via a wireless link. In an example, the electrostimulation circuit 220 may be part of the wireless pacing units.

The electrostimulation circuit 220 may be configured to generate HBP pulses for stimulating a target site at or near the His bundle via one or more of the electrodes 201. In an example, the electrostimulation circuit 220 may be configured to deliver unipolar HBP, where the stimulation energy (current or voltage) is applied between one of the electrodes 112A-112B (e.g., as a cathode) and a reference electrode such as the housing 116 (e.g., as an anode). In another example, the electrostimulation circuit 220 may be configured to deliver bipolar HBP, where the stimulation energy is applied between two electrodes at or near the His bundle, such as between the electrodes 112A and 112B. In an example, the electrostimulation circuit 220 may be configured to deliver extended bipolar HBP, where the stimulation energy is applied between a pair of electrodes each selected from a separate lead, such as between a first electrode selected from the electrodes 112A-112B associated with the lead 106 and a second electrode selected from of the proximal electrodes 131A-131B associated with the lead 107.

The electrostimulation circuit 220 may generate LVP pulses for stimulating at least one epicardial or endocardial LV site via one or more of the electrodes 201, such as one or more distal electrodes 132A-132C associated with the lead 107. In an example, the electrostimulation circuit 220 may be configured to deliver pacing pulses at a signal LV site, also known as single-site pacing (SSP). Alternatively, in some examples, the electrostimulation circuit 220 may be configured to deliver multisite pacing (MSP) such that two or more LV sites are simultaneously stimulated, or sequentially stimulated with a specified inter-site pacing delay, within the same cardiac cycle.

The electrostimulation circuit 220 may deliver the LVP pulses to a target site (the target site in SSP, or one of multiple target sites in MSP) using one of pacing configurations including, for example, a unipolar, a bipolar, or a tripolar LV pacing. Unipolar LVP refers to an application of stimulation energy (current or voltage) between one of the distal electrodes 132A-132C (e.g., as a cathode) and the housing 116 (e.g., as an anode). Bipolar LVP refers to an application of stimulation energy between two electrodes positioned at or near the LV epicardium or endocardium, such as between two of the electrodes 132A-132C, where one is designated as an anode and the other designated as an anode. In an example, LVP pulses may be delivered using a pace vector consisting of a first electrode (e.g., the cathode) being an LV electrode such as selected from the distal electrodes 132A-132C, and a second electrode (e.g., the anode) being an electrode positioned on a cardiac site other than the left ventricle, such as an RA electrode selected from the proximal electrodes 131A-131B, a His bundle electrode 112A-112B, or an RV electrode (not shown). This pacing configuration is hereinafter referred to as an extended bipolar LVP. In another example, a tripolar LVP configuration may be used, which involves two LV electrodes used jointly as the cathode, or two electrodes such as selected from the RA and RV electrodes used jointly as the anode.

In various examples, the electrostimulation circuit 220 may be configured to stimulate an atrium, such as to generate right atrial pacing (RAP) pulses or left atrial pacing (LAP) pulses for delivery at or near an atrial site via one or more of the electrodes 201, such as one or more proximal electrodes 131A-131B associated with the lead 107.

The control circuit 230 may control the delivery of the pacing pulses to one or more target sites, including HBP at or near the His bundle, and LVP at a left ventricular target site. In an example, the control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a capture verification circuit 232, a timing circuit 234, an HBP control circuit 235, and an LVP control circuit 236. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The capture verification circuit 232 may be configured to verify His-bundle capture status using one or more physiologic signals sensed by the sensing circuitry 210. The His-bundle capture status indicates whether the HBP pulses, when delivered at or near a His bundle, causes direct excitation (depolarization) of the excitatory fibers of the His bundle. In some cases, HBP pulses may directly cause substantial excitation of the muscle tissue adjacent to the His bundle (also known as the para-Hisian myocardium). By detecting direct His-bundle activation and para-Hisian myocardial excitation, the capture verification circuit 232 may further classify the His-bundle capture status into one of capture types, such as a selective His-bundle capture, non-selective His-bundle capture, para-Hisian capture, or loss of capture. The selective His-bundle capture refers to an excitation (depolarization) of only the His bundle without excitation of the unintended and undesirable para-Hisian myocardium directly resulting from the HBP pulses. The non-selective His-bundle capture refers to excitation of both the His bundle and the para-Hisian myocardium directly resulting from the HBP pulses. The para-Hisian capture refers to only the unintended and undesirable excitation of the para-Hisian myocardium without excitation of the His bundle directly resulting from the HBP pulses. If neither the para-Hisian myocardium nor the His bundle is excited by the HBP pulses, then a loss of capture is indicated.

In an example, the capture verification circuit 232 may determine the His-bundle capture status using a physiologic signal sensed from the left ventricle in response to the delivery of HBP pulses. Left-ventricular activity, such as an LV depolarization (referred to as an LV sense event, or LVS), may be detected from an LV EGM sensed by the left-ventricular sensing circuit 216. In an example, His-bundle capture status may be determined using timing information of the LVS event, such as a paced His-to-left ventricular (Hp-LV) interval representing a time delay from the HBP pulse delivery to the sensed LVS event. Generally, direct His-bundle capture (as in both selective His-bundle capture and non-selective His-bundle capture) may be characterized by a shorter Hp-LV interval due to faster propagation of the His bundle depolarization through the natural His-Purkinje system. In contrast, para-Hisian myocardial capture without direct His-bundle capture (as in para-Hisian capture status) may be characterized by a relatively longer Hp-LV interval due to relatively slower, muscle-to-muscle conduction of the depolarization wave through the myocardium. In an example, the capture verification circuit 232 may decide that a His bundle capture (selective or non-selective) has occurred if the Hp-LV interval falls below a threshold ($HV_{TH}$), and that a para-Hisian capture has occurred if the Hp-LV interval exceeds the threshold $HV_{TH}$. The threshold $HV_{TH}$ may be determined using an intrinsic delay from a His-bundle sensed event to an LVS event.

In an example, the capture verification circuit 232 may detect His-bundle capture status using a capture detection window ($W_D$) that begins at the delivery of an HBP pulse, and has a specified window length. The capture verification circuit 232 may decide that a direct His bundle capture (selective or non-selective) has occurred if an LVS event is detected within the window $W_D$, and no direct His bundle capture has occurred if no LVS event is detected within the window $W_D$. The window length may be programmed to a value equal to or less than the threshold $HV_{TH}$. In an example, the window length is approximately 50-120 milliseconds (msec). In some examples, the window length may be at least partially automatically determined and dynamically updated based on patient historical data of His-bundle capture status, such that the window length is longer than the Hp-LV interval corresponding to historical His-bundle capture (selective or non-selective capture), and shorter than the Hp-LV interval corresponding to historical para-Hisian capture.

In another example, the capture verification circuit 232 may compare the Hp-LV interval to an intrinsic His-to-left ventricular (Hs-LV) interval. The Hs-LV interval represents a time delay from an intrinsic His bundle activity (Hs) to the sensed LVS event. The intrinsic His bundle activity may be detected in response to an intrinsic sinus node firing during a sinus rhythm, or in response to an atrial pacing (AP) event. If the Hp-LV interval does not differ from the Hs-LV interval by at least a specified margin, then the capture verification circuit 232 determines that a selective His bundle capture has occurred, which results in fast conduction from the His bundle to the left ventricle. However, if the Hp-LV interval exceeds the Hs-LV interval by more than the specified margin, then the conduction is deemed slow, and a non-selective His bundle capture or a para-Hisian capture is indicated.

In some examples, the capture verification circuit 232 may determine the His-bundle capture status using a morphology of an LVS event. The morphology may be extracted from an LV EGM Examples of the morphological features may include a QRS width, a slope of the upstroke or down-stroke branch of the R wave, or an area under the QRS curve, among others. Due to the different conduction pathways involved and different conduction properties (e.g., velocity), His-bundle capture and para-Hisian capture may result in distinct ventricular EGM morphologies. A His-bundle capture is generally characterized by a narrower QRS complex due to fast conduction and more coordinated contraction of the left and right ventricles. A para-Hisian capture is generally characterized by a wider QRS complex due to relatively slower muscle-to-muscle conduction, and less coordination between the left and right ventricles. In an example, the left-ventricular sensing circuit 216 may sense a unipolar LV EGM between an LV electrode (e.g., one of the distal electrodes 132A-132C associate with the lead 107) and a reference electrode (e.g., the housing 116 of the IMD 104). A unipolar LV EGM may represent a more global perspective to the activation of the heart than a bipolar LV EGM that represents a localized myocardial depolarization. In some examples, an array of electrodes on the housing 116 may be electrically connected to increase the area of electrode-tissue interface.

In an example, the capture verification circuit 232 may detects His-bundle capture status using QRS width measurement from an LV EGM. The capture verification circuit 232 may decide that a His-bundle capture has occurred if the QRS width falls below a width threshold, or a para-Hisian myocardial capture, absent of direct para-Hisian capture, has occurred if the measured QRS widths exceeds the width threshold. The width threshold may be programmed to a value such as to better distinguish slower muscle-to-muscle myocardial response from faster His-bundle response. In an example, the width threshold is approximately 90-120 msec. In another example, the width threshold is approximately 120-140 msec. In an example, the width threshold may be at least partially automatically determined and dynamically updated based on patient historical HBP capture data, such as QRS width measured during historical His-bundle capture and QRS width measured during historical para-Hisian myocardial capture.

In an example, the capture verification circuit 232 may determine the His-bundle capture status using a far-field ventricular activity of the heart in response to the HBP pulses. In contrast to direct ventricular activity sensed via electrodes positioned on a ventricular (such as the LV EGM as discussed above), the far-field ventricular activity may be sensed from a site other than the ventricles. In an example, the far-field ventricular activity may be detected from an atrial EGM, such as sensed by the atrial sensing circuit 212. In another example, the far-field ventricular activity may be detected from a His-bundle EGM, such as sensed by the His-bundle sensing circuit 214. In some examples, the capture verification circuit 232 may determine the His-bundle capture status using a near-field para-Hisian myocardial EGM and a far-field cardiac EGM. The near-field para-Hisian myocardial EGM may be sensed within a first time window using a bipolar sense vector comprising two electrodes at or near the His bundle (e.g., electrodes 112A and 112B). The far-field cardiac EGM may be sensed within a second time window using a unipolar sense vector comprising an electrode at or near the His bundle (e.g., one of the electrode 112A or 112B) and a reference electrode distal to the His bundle (e.g., housing 116, or one or more electrodes on the housing 116). Capture verification and capture type classification using far-field cardiac activity, such as described by commonly assigned U.S. Provisional Patent Application Ser. No. 62/580,711, entitled "SYSTEMS AND METHODS FOR HIS-BUNDLE PACING", filed on Nov. 2, 2017, are incorporated herein by reference in its entirety.

The capture verification circuit 232 may determine the capture status using one or more mechanical or hemodynamic sensors, including detecting the His bundle response and myocardial response, or classifying a tissue response into one of capture types. Zhu et al. U.S. Pat. No. 8,688,234, entitled "DEVICES, METHODS, AND SYSTEMS INCLUDING CARDIAC PACING," refers to determining the effectiveness or completeness of His-bundle capture using attributes of a QRS signal, such as QRS narrowing, or using mechanical or hemodynamic sensors, the disclosure of which is incorporated herein by reference in its entirety. Dong et al. U.S. Pat. No. 8,565,880 entitled "HIS-BUNDLE CAPTURE VERIFICATION AND MONITORING," refers to His-bundle capture verification using hemodynamic sensors such as heart sound or blood pressure sensors, the disclosure of which is incorporated by reference herein in its entirety.

The timing circuit 234 may be configured to time the delivery of electrostimulation to the heart. In an example, the timing circuit 234 may time the delivery of an HBP pulse in a cardiac cycle using an atrial-to-His bundle (AH) interval. The AH interval represents a programmable interval from an intrinsic atrial event (AS) or a paced atrial event (AP), such as detected by the atrial sensing circuit 212 from an atrial EGM, to the delivery a HBP pulse. In an example, the AH interval may be programmed to approximately 50 msec shorter than a sensed P wave-to-R wave (PR) interval or a programmed atrial-to-ventricular (AV) delay within a cardiac cycle. In various examples, a user may program an AV delay and an HV interval, such that that AH interval may be determined as AH=AV−HV. The HV interval may be programmed to approximately 50-80 msec, which determines how far in advance to the end of the AV delay that the HBP pulse is delivered. The AV delay may be a sensed AV delay between an AS event and a ventricular pacing pulse in the same cardiac cycle, or a paced AV delay between an AP event and a ventricular pacing pulse in the same cardiac cycle. The paced AV delay may be programmed to be slightly longer to allow for atrial pace latency and intra-atrial conduction delay. The timing circuit 234 may also time the delivery of an LVP pulse in a cardiac cycle using one or more programmable timing parameters associated with left-ventricular single site pacing (SSP) or multi-site pacing (MSP). Examples of the programmable timing parameters include an atrial-ventricular delay (AVD) representing a latency period from an AS event or an AP event to an LVP pulse, or an intra-ventricular pacing delay representing a time delay between pacing at multiple LV sites. The timing parameters for HBP and LVP may be programmed via the user interface 240.

The HBP control circuit 235 is coupled to the electrostimulation circuit 210 to control the delivery of HBP pulses according to the timing information provided by the timing circuit 234, and one or more stimulation parameters. The HBP control circuit 235 may adjust one or more stimulation parameters for HBP based on the His-bundle capture status or the classified capture types, such that the HBP may more effectively capture the His bundle and activate the natural His-Purkinje conduction system. The parameter adjustment may be initiated periodically at specified time period, or triggered by a specific event, such as a detection of an absence of direct His-bundle capture (e.g., para-Hisian myocardial capture, or loss of capture). For example, if no direct His-bundle capture is detected, the HBP control circuit 235 may adjust stimulation strength (e.g., one or more of pulse amplitude, pulse width, pulse frequency, pulse waveform, duty cycle, or stimulation duration), or stimulation timing (e.g., the AH interval). Alternatively or additionally, the HBP control circuit 235 may adjust a stimulation site, such as by switching to a different HBP vector including an electrode in close proximity to the His bundle to improve the likelihood of selective His-bundle capture. In an example, the HBP control circuit 235 may switch from a bipolar HBP vector (e.g., using electrodes 112A and 112B) to an extended bipolar HBP vector as defined between a first electrode (e.g., a cathode) selected from the electrodes 112A-112B associated with the first lead 106, and a second electrode (e.g., an anode) selected from the proximal electrodes 131A-131B, or from the distal electrodes 132A-132C, associated with the second lead 107. The HBP control circuit 235 may select the second electrode from the lead 107 based on spatial proximity to the first electrode on the lead 106. Alternatively, the second electrode may be selected based on a spatial proximity to a septum between ventricles of the heart. For example, an extended bipolar HBP vector may include the electrode 112B on the lead 106 as a cathode, and the electrode 131A on the lead 107 because it is spatially closer to the His-bundle electrode 112B, or because it is spatially closer to the septum. Such an extended bipolar vector may steer the electric field deeper across the membranous septum, thus increase the likelihood of His-bundle capture or recruitment of blocked conduction fibers.

The parameter adjustment may be automatically executed. Alternatively, a user (e.g., a clinician) may confirm or modify the adjustment, such as using the user interface 240. The parameter adjustment may be continued until the capture verification circuit 232 detects a direct His-bundle capture produced by the adjusted HBP.

The LVP control circuit 236 is coupled to the electrostimulation circuit 210 to control the delivery of LVP pulses according to the timing information provided by the timing circuit 234, and one or more stimulation parameters. The stimulation parameters may be determined using the His-bundle capture status detected by the capture verification circuit 232. The delivery of LVP pulses may be conditional upon the His-bundle capture status. In an example, the LVP pulses may be delivered concurrently with the HBP pulses. In another example, the LVP and HBP pulses may be delivered sequentially, such that the LVP pulses are delivered after a time delay subsequent to the delivery of HBP pulses. Examples of controlling the LVP are discussed below, such as with reference to FIGS. 3-4.

In various examples, the control circuit 230 may include a pacing threshold test circuit (not shown) configured to determine a pacing threshold representing minimal energy required to excite the His bundle. The HBP control circuit 235 may adjust one or more stimulation parameters using the determined pacing threshold. The pacing threshold may be determined during implant of the IMD 104, periodically at specified time period, or triggered by a specific event such as an absence of direct His-bundle capture or a user command. The threshold test may include delivering HBP pulses (e.g., via the electrostimulation circuit 220) at or near the His bundle in accordance with a threshold test protocol that defines varying a stimulation parameter at a specified manner, such as ramping up or ramping down the pulse amplitude. In an example, the capture verification circuit 232 may measure time intervals (HV interval) between the delivery of HBP pulses with varying pulse amplitude and the corresponding LVS event detected within a capture detection window ($W_D$). The threshold test circuit may detect a step change in the measured HV interval in response to the delivery of the HBP pulses with varying pulse amplitude. For example, a step increase in HV interval indicates a transition from a propagatable His-bundle excitation to a para-Hisian myocardium only excitation without His-bundle capture. The threshold test circuit may determine the pacing threshold to be the pulse amplitude corresponding to the detected step change in the measured HV interval. In an example, the pulse amplitude is decremented on every 3-5 beats, until the threshold test circuit detects a step increase in the measured HV interval by at least 30 msec. The threshold test circuit may determine the pacing threshold to be the highest pulse amplitude that results in the detected step increase in the measured HV interval. The HBP control circuit 235 may adjust the stimulation strength, such as pacing amplitude, based on the pacing threshold. In an example, the pacing amplitude may be adjusted to be 3-5 times the pacing threshold for an improved performance of His-bundle capture. Additionally or alternatively, the threshold test circuit may determine the pacing threshold using a morphology of the LVS event, or a morphology of a far-field ventricular response, such as a change in QRS wave width. Threshold test for HBP based on HV interval or ventricular or far-field morphology, such as described by commonly assigned U.S. Provisional Patent Application Ser. No. 62/580,711, entitled "SYSTEMS AND METHODS FOR HIS-BUNDLE PACING", filed on Nov. 2, 2017, are herein incorporated by reference in its entirety.

The user interface 240 may include an input unit and an output unit. In an example, at least a portion of the user interface 240 may be implemented in the external system 140. The input unit may receive user input such as values of the parameters for sensing physiologic event sensing, and parameters for detecting His-bundle capture status. The user input may receive user programming of stimulation parameters, or confirmation, rejection, or otherwise modification of the stimulation parameters. The input unit may include an input device such as a keyboard, on-screen keyboard, mouse, trackball, touchpad, touch-screen, or other pointing or navigating devices. The output unit may include circuitry configured to generate a human-perceptible notification of His-bundle capture status or classification of capture types. The output circuit may be coupled to a display for displaying the received physiologic signals, including tracings of one or more of atrial EGM. His-bundle EGM. LV EGM, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the His-bundle capture status. In an example, the output unit may generate an alert when a loss of capture is indicated and a backup pacing is delivered. In another example, if the backup pacing delivery is found to be frequent (e.g., when the backup pacing in response to an absence of direct His-bundle capture is activated for a number of times exceeding a threshold within a time period), then it may trigger the output unit to generate an alert and prompt a user (e.g., a clinician) to reprogram the pacing system.

Figure 3:
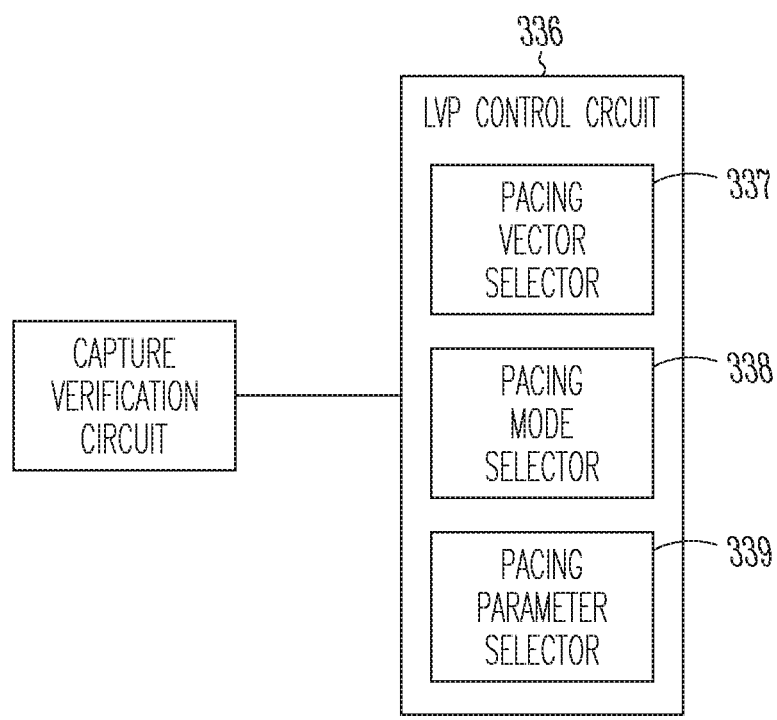
FIG. 3 illustrates generally an example of a circuit for controlling left-ventricular pacing (LVP) based on the His-bundle capture status.

FIG. 3 illustrates generally an example of LVP control circuit 336 for controlling LVP delivery based on the His-bundle capture status. The LVP control circuit 336, which is an embodiment of the LVP control circuit 236 of FIG. 2, may include one or more of a pace vector selector 337, a pacing mode selector 338, and a pacing parameter selector 339.

The pace vector selector 337 may select or adjust an LVP vector for delivering LVP pulses based at least on the His-bundle capture status. The selection or adjustment of the LVP vector may include switching to a different electrode as an anode or a cathode of an LVP vector, switching from a uni-polar pacing configuration to a bi-polar pacing configuration, or switching from a bi-polar pacing configuration to an extended bipolar pacing configuration, among others. The pacing mode selector 338 may select or adjust an LV pacing mode, such as switching from a single-site pacing (SSP) mode to a multisite pacing (MSP) mode to stimulate two or more LV sites simultaneously or sequentially with a specified inter-site pacing delay within the same cardiac cycle. The pacing parameter selector 339 may select or adjust one or more parameters associated with amount of energy including, for example, pulse amplitude, pulse width, pulse frequency, pulse waveform, duty cycle, or stimulation duration, among others.

In an example, the pacing parameter selector 339 may select parameters corresponding to higher LV stimulation energy than conventional pacing pulses, which is referred to as high-output pacing (HOP). The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, HOP may increase myocardial contractility and improve systolic function. To prevent potentially hazardous overstressing of the heart associated with chronic HOP, the HOP pulses may be delivered on an intermittent basis. For example, the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

Figure 4:
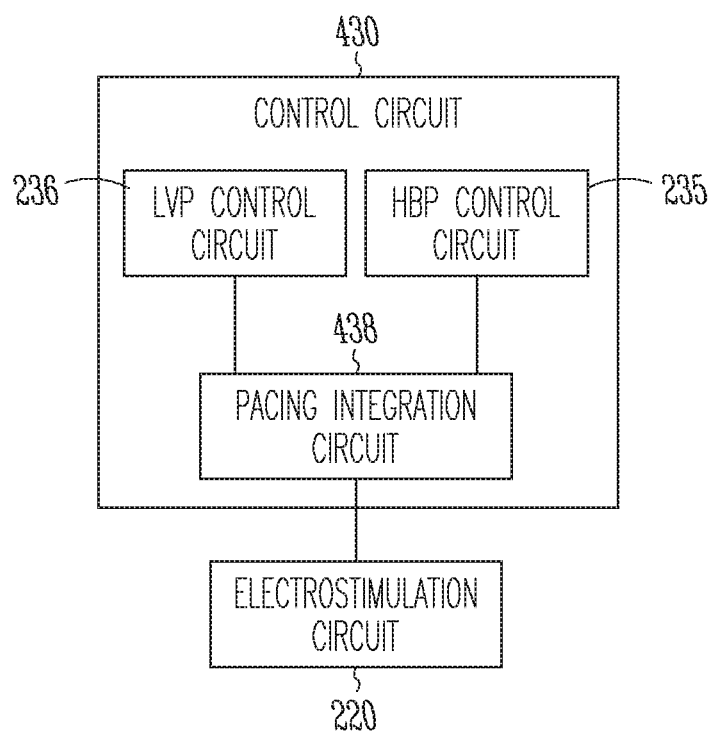
FIG. 4 illustrates generally an example of portions of a pacing control circuit for controlling integrated His-bundle pacing (HBP) and LVP.

In various examples, the LVP control circuit 336 may select or adjust one or more of the LV pace vector, pacing mode, or one or more pacing parameters based on a degree of normalization of the QRS duration in response to the delivery of HBP, or in response to integrated HBP and LVP either concurrently or sequentially delivered, as to be discussed in FIG. 4. The LVP control circuit 336 may compare the QRS duration to a threshold, or to a reference QRS duration corresponding to depolarization conducted through an intact His-Purkinje system. In an example, in response to the degree of QRS prolongation, the pacing parameter selector 339 may increase stimulation strength, the pace vector selector 337 may switch to an LVP vector including an electrode (e.g., electrode 132A) positioned at an LV site with later depolarization as opposed to an LV site with earlier depolarization, or the pacing mode selector 338 may switch from a SSP mode to a MSP mode. The parameter adjustment may be automatically executed. Alternatively, a user (e.g., a clinician) may confirm or modify the adjustment via a user interface 240.

FIG. 4 illustrates generally an example of at least a portion of a pacing control circuit 430 for controlling integrated HBP and LVP. The pacing control circuit 430, which is an embodiment of the control circuit 230 of FIG. 2, may include, among other components, the HBP control circuit 235, the LVP control 236, and a pacing integration circuit 435. The LVP control circuit 236 is configured to control the electrostimulation circuit 220 to deliver LVP pulses subsequent to the delivery of the HBP pulse and within the same cardiac cycle. The LVP pulses may serve as backup therapy to excite the myocardium and to prevent asystole following an unsuccessful HBP. In an example, the backup LVP pulses may be delivered if a loss of capture is indicated, characterized by neither the para-Hisian myocardium capture nor the His-bundle capture by the delivery of HBP pulses within the capture detection window $W_D$. In another example, the backup LVP pulses may be delivered if a para-Hisian myocardium capture, in absence of direct His-bundle capture, is detected. The LVP may be delivered immediately following the end of a His-bundle capture detection window within which no direct His-bundle capture is detected. The LVP thus delivered is within the same cardiac cycle as the HBP. In another example, the LVP pulse may be delivered in a delayed fashion after a specific number of non-direct His-bundle capture beats. For example, backup LVP may be delivered if at least five non-direct His-bundle capture beats have been detected, or if at least five out of seven non-direct His-bundle capture beats have been detected.

The pacing integration circuit 438 may control the electrostimulation circuit 220 to deliver an integrated HBP and LVP. In an example, the LVP pulses may be delivered concurrently with the delivery of the HBP pulse. In another example, the LVP pulse may be delivered subsequent to the delivery of the HBP pulse after a specific time delay. The LVP pulse may be delivered irrespective of the His-bundle capture status, or may alternatively be delivered only if the His-bundle capture status satisfies a specific condition (e.g., a loss of capture, or a para-Hisian myocardium capture in absence of direct His-bundle capture). In some patients with cardiac conduction abnormality (such as bundle branch block), although the HBP can correct conduction block at the His bundle site to some extent, the HBP may not always result in complete normalization of the QRS duration. This is likely because the block in the proximal part of the His-Purkinje system may have been resolved with HBP, but there may be additional conduction slowing peripherally in the terminal fibers of the His bundle, or fibers extending from endocardial to epicardial layers. As such, at least in some patients, even a selective His-bundle capture and an activation of the His-Purkinje system may not produce adequate cardiac synchrony to the same extent as with an intact His-Purkinje system. Compared to conventional cardiac pacing at one or both ventricles, concurrent or sequential pacing at both the His bundle and the left ventricle, as discussed in the present document, may help further improve ventricular synchrony and overall cardiac performance in these patients.

Figure 5:
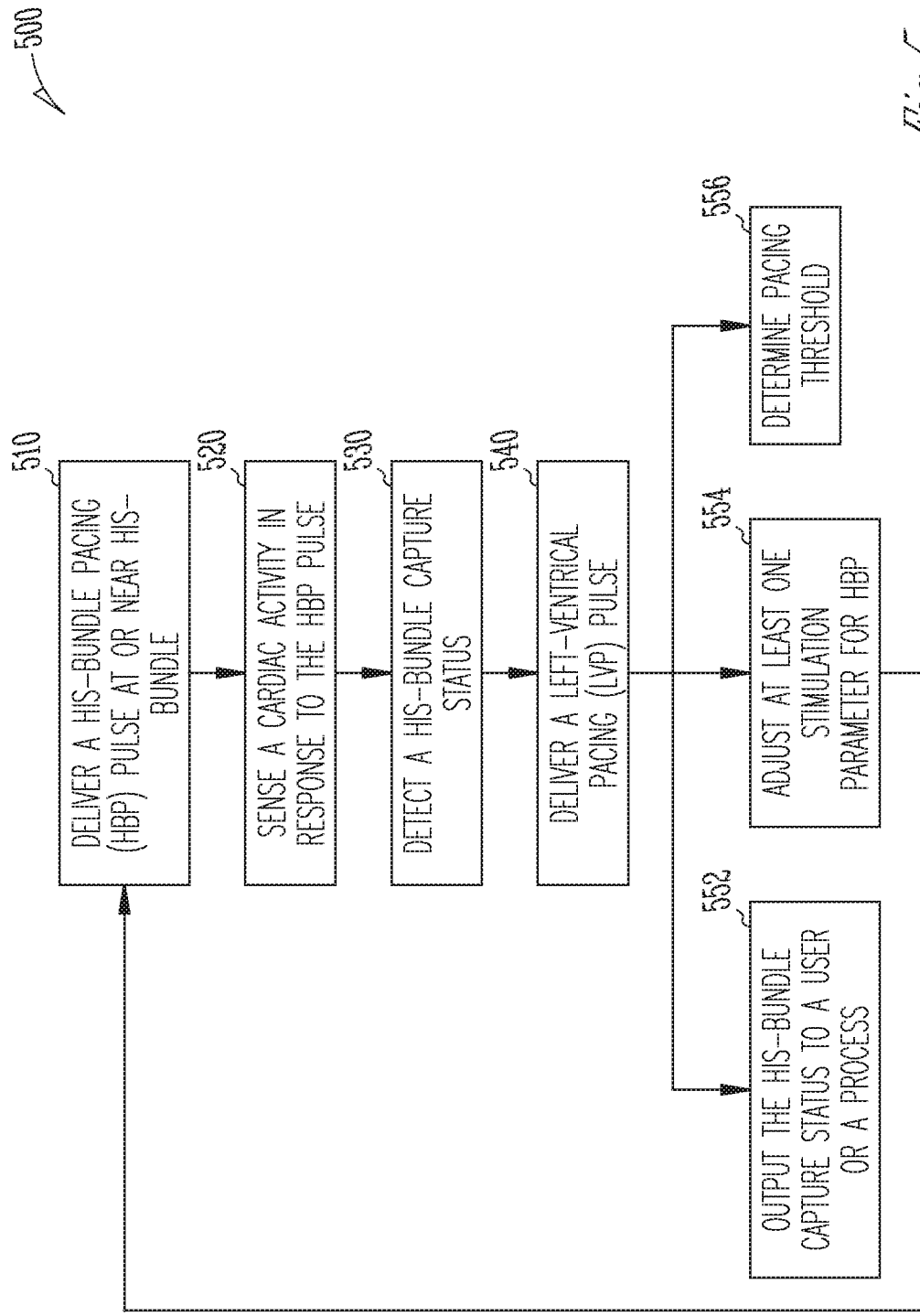
FIG. 5 illustrates generally an example of a method for operating a cardiac pacing system to deliver cardiac pacing to a patient.

FIG. 5 illustrates generally an example of a method 500 for operating a cardiac pacing system to deliver cardiac pacing to a patient. The method 500 may be implemented and executed in an ambulatory medical device such as an implantable or wearable medical device, or in a remote patient management system. In an example, the method 500 may be implemented in, and executed by, the an IMD (e.g., the IMD 104) electrically coupled to at least a first lead (e.g., the lead 106) associated with one or more His-bundle electrodes and a second lead (e.g., the lead 107) associated with one or more left-ventricular electrodes and one or more atrial electrodes. In some examples, at least a portion of the method 500 may be implemented in, and executed by, devices in the external system 140, or the cardiac pacing system 200.

The method 500 commences at 510, where a His-bundle pacing (HBP) pulse may be generated and delivered to a target site. The target site may include a region at or near the His bundle 121, such as a region distal to the blocked or slowly conducting AV node and in the AV septum, an interventricular septum region, or a right atrial region near the His-bundle 121. The HBP pulse may be generated by the electrostimulation circuit 220, according to one or more stimulation parameters. Examples of the stimulation parameters may include stimulation site, stimulation timing, or stimulation strength, among other parameters. The HBP pulses may be delivered via a delivery system including, for example, the lead 106 associated with one or more of the electrodes 112A-112B. In an example, the HBP pulse may be delivered in response to an intrinsic cardiac depolarization or an atrial pace event, as to be discussed in the following with reference to FIG. 6.

At 520, a cardiac activity is sensed in response to the HBP pulse delivery. The cardiac activity may be sensed using one or more physiologic sensors or electrodes coupled to sensing circuitry, such as sensing circuitry 210. Examples of the physiologic signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others. In some examples, the cardiac activity may be presented in a far-field cardiac electrical signal representing ventricular response to the delivery of the HBP pulses. A far-field cardiac electrical signal may provide a global perspective to the activation of the heart. In an example, the far-field cardiac electrical signal may be sensed using a unipolar sense vector comprising an electrode disposed at or near the His bundle (e.g., one of the electrodes 112A-112B) or in an atrium (e.g., one of the proximal electrodes 131A-131B), and a reference electrode distal to the His bundle, such as the housing 116 of the IMD 104. In another example, the far-field cardiac electrical signal may be sensed using a bipolar sense vector comprising two electrodes disposed at or near the His bundle or in an atrium.

At 530, a His-bundle capture status may be detected. The His-bundle capture status indicates whether the HBP pulse, when delivered at or near a His bundle, causes direct excitation (depolarization) of the excitatory fibers of the His bundle. In some cases, the HBP pulse may directly cause substantial excitation of the muscle tissue adjacent to the His bundle (also known as the para-Hisian myocardium). By detecting direct His-bundle activation and para-Hisian myocardial excitation, the His-bundle capture status may be further classified into one of capture types, such as a selective His-bundle capture, non-selective His-bundle capture, para-Hisian capture, or loss of capture.

His-bundle capture status may be detected using one or more of timing information or morphology of a sensed cardiac activity. Examples of the His-bundle capture status detection using LV activity such as an LV EGM is discussed below, such as with reference to FIG. 6. Additionally or alternatively, His-bundle capture status may be detected using a far-field ventricular activity such as from an atrial EGM or from a His-bundle EGM. In some examples, His-bundle capture status may be detected using both a near-field para-Hisian myocardial EGM and a far-field cardiac EGM, such as described by commonly assigned U.S. Provisional Patent Application Ser. No. 62/580,711, entitled "SYSTEMS AND METHODS FOR HIS-BUNDLE PACING", filed on Nov. 2, 2017, the disclosure of which is herein incorporated by reference in its entirety. In various examples, His-bundle capture status may be detected further using one or more mechanical or hemodynamic sensors such as heart sound or blood pressure sensors, such as described by commonly assigned U.S. Provisional patent application Ser. No. 8/565,880, entitled "HIS-BUNDLE CAPTURE VERIFICATION AND MONITORING," the disclosure of which is incorporated by reference herein in its entirety.

At 540, left-ventricular pacing (LVP) pulses may be delivered to one or more epicardial or endocardial LV sites, such as via one or more distal electrodes 132A-132C associated with the lead 107. The LVP may be delivered at a signal LV site (i.e., single-site pacing, or SSP), or at multiple LV sites (multisite pacing, or MSP). During MSP, the LVP pulses may be delivered at the multiple LV sites simultaneously, or sequentially with a specified inter-site pacing delay, within the same cardiac cycle. At each LV site, the LVP pulses may be delivered using a unipolar, a bipolar, an extended bipolar, or a tripolar LV pace vector.

The LVP pulses may be delivered according to one or more stimulation parameters controlling the amount of energy to be delivered to the one or more LV sites. The LVP pulses may be delivered at specific time with respect to the HBP pulse delivery. In an example, the delivery of LVP pulses may be conditional upon the His-bundle capture status. In some examples, the LVP pulses may be delivered concurrently with the HBP, or in a sequential mode subsequent to the delivery of HBP pulses. The LVP pulses may be delivered irrespective of the His-bundle capture status, or may alternatively be delivered only if the His-bundle capture status satisfies a specific condition. Examples of methods for delivering LVP are discussed below, such as with reference to FIG. 6.

The His-bundle capture status and optionally the classified capture types may be output to a user (e.g., a clinician) or a process at 552, such as being displayed on a display of the user interface 240. The sensed cardiac signals (e.g., atrial, His-bundle, or LV EGMs or other physiologic signals), timing or morphological information of the sensed cardiac signals, or the programmed stimulation parameters, among other intermediate measurements or computations, may also be displayed.

In some examples, the His-bundle capture status may be used to adjust at least one stimulation parameter for HBP at 554, such as via the HBP control circuit 235. The stimulation parameter adjustment may be performed when the His-bundle capture status indicates a para-Hisian myocardial capture without direct His-bundle capture, or as a loss of capture such that neither His-bundle nor the para-Hisian myocardium is captured. In some examples, stimulation parameter adjustment may be based on capture statistics computed using the capture verification and classification results over multiple heart beats. Examples of the capture statistics may include percentages, histograms, or other measures of distribution of the selective His-bundle capture, non-selective His-bundle capture, or para-Hisian capture. The stimulation parameter adjustment may be performed when the capture statistics satisfy a specific condition. In various examples, the parameter adjustment may include switching to a different stimulation site, using a different pace vector configuration, adjusting the AH interval with respect to an intrinsic or paced atrial activation, adjusting stimulation strength such as one or more of pulse amplitude, pulse width, pulse frequency, pulse waveform, duty cycle, or stimulation duration. HBP pulses may be generated and delivered at 510, according to the adjusted stimulation parameters to more effectively capture the His bundle, activate the natural conduction pathway, and improve patient cardiac performance.

The His-bundle capture status may additionally or alternatively be used to guide a pacing threshold test to determine a proper His-bundle pacing threshold at 556, such as by using the threshold test circuit. The pacing threshold represents minimal energy required to excite the His bundle. In an example, the pacing threshold test may be triggered by a loss of capture or a para-Hisian myocardial capture, in which no His-bundle capture is achieved directly by the HBP pulses.

Additionally or alternatively, the pacing threshold test may be carried out at the implant of the IMD 104, periodically at specified time period, or upon receiving a user command. The pacing threshold test may include delivering a series of HBP pulses with varying pulse amplitude, such as HBP pulses with decreasing amplitudes in a ramp-down test or HBP pulses with increasing amplitudes in a ramp-up test. Time intervals (HV intervals) between the delivery of HBP pulses and the corresponding sensed far-field ventricular activities (e.g., far-field R waves) may be measured. The pacing threshold may be determined as the pulse amplitude corresponding to a step change in the measured HV intervals, such as a step increase in the measured HV intervals in a ramp-down test. The step change in the HV intervals indicates a transition from a propagatable His-bundle excitation to a local para-Hisian myocardial excitation without His-bundle capture. In some other examples, the pacing threshold test may additionally be based on a change in morphology of an LVS event, or a morphology of a far-field ventricular response, such as a change in QRS wave width.

Figure 6:
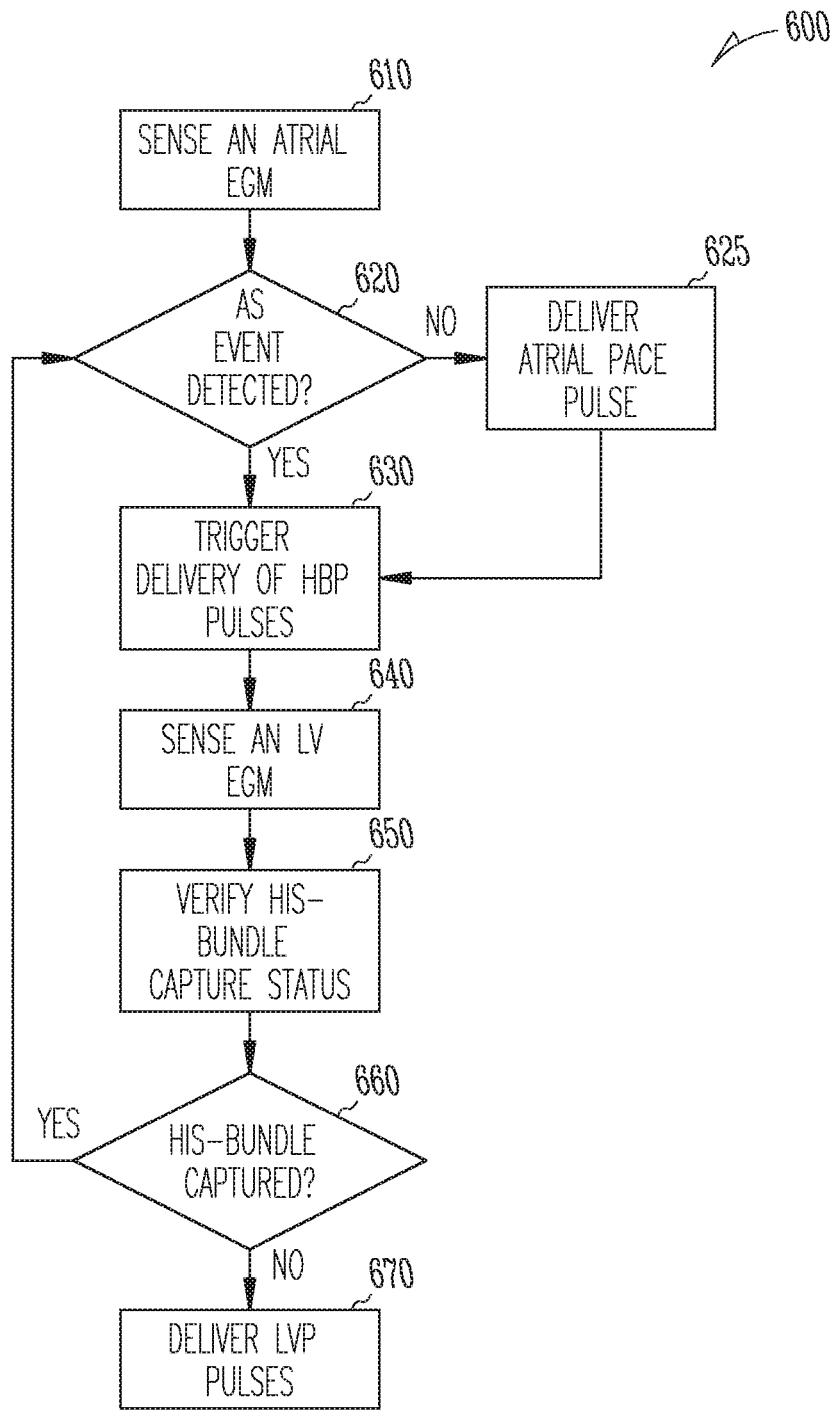
FIG. 6 illustrates an example of a method for operating a cardiac pacing system to deliver HBP and LVP to a patient.

FIG. 6 illustrates an example of a method 600 for operating a cardiac pacing system to deliver HBP and LVP to a patient, such as using the IMD 104 coupled to at least a first lead 106 and a second lead 107. The method 600 may be an embodiment of the method 500. The method 601 commences at 610 where an atrial EGM may be sensed, such as by using the atrial sensing circuit 212 and one or more of the proximal electrodes 131A-131B associated with the lead 107. At 620, an intrinsic atrial activation event (referred to as an AS event) may be detected from the atrial EGM. If no AS event is detected, then an atrial pacing pulse may be delivered at 625. The atrial pacing pulse may be delivered using the electrostimulation circuit 220 and one or more proximal electrodes 131A-131B associated with the lead 107.

At 630, the AS event detected at 620 or the AP event detected at 625 may trigger generation of a His-bundle pacing (HBP) pulse. The HBP pulse may be generated according to one or more HBP stimulation strength parameters including, for example, a pulse amplitude, a pulse width, a pulse frequency, a pulse waveform, a duty cycle, or a stimulation duration. The HBP pulse may be delivered in a unipolar, bipolar, extended polar, or tripolar configuration, among others. In an example, an extended bipolar HBP vector may consist of a first electrode (e.g., a cathode) selected from the electrodes 112A-112B associated with the first lead 106 and a second electrode (e.g., an anode) selected from the proximal electrodes 131A-131B associated with the second lead 107. The second electrode may be automatically selected from multiple proximal electrodes on the lead 107 based on spatial proximity to the first electrode on the lead 106. Alternatively, the second electrode may be selected based on a spatial proximity to a septum between ventricles of the heart. By way of example, an extended bipolar HBP vector may include the electrode 112B as the cathode, and the electrode 131A as the anode. Such an extended bipolar vector may steer the electric field deeper across the membranous septum, thus increase the likelihood of His-bundle capture.

At 640, an LV EGM is sensed, such as by using the left-ventricular sensing circuit 216 and one or more of the distal electrodes 132A-132C associated with the lead 107. The LV EGM is sensed in response to the HBP pulse delivery. In an example, the LV EGM may be sensed using a bipolar sense vector between two LV electrodes such as selected from the distal electrodes 132A-132C associated with the lead 107. In an example, the LV EGM may be sensed using a unipolar sense vector between one LV electrode (e.g., one of the distal electrodes 132A-132C) and a reference electrode (e.g., the housing 116 of the IMD 104).

At 650, the LV EGM may be used to determine His-bundle capture status. In an example, the His-bundle capture status may be determined using timing information of an LVS event detected from the LV EGM. The LVS timing may be determined from a bipolar LV EGM that represents a localized myocardial depolarization. A paced His-to-left ventricular (Hp-LV) interval representing a time delay from the HBP pulse delivery to the sensed LVS event. A His bundle capture (selective or non-selective) has occurred if the Hp-LV interval falls below a threshold ($HV_{TH}$), and that a para-Hisian capture has occurred if the Hp-LV interval exceeds the threshold $HV_{TH}$. Generally, direct His-bundle capture results in a faster propagation through the His-Purkinje system, and therefore a shorter Hp-LV interval. In contrast, para-Hisian myocardial capture generally results in slower, muscle-to-muscle conduction, and therefore a relatively longer Hp-LV interval. The His-bundle capture status may be determined using a capture detection window ($W_D$). In an example, the window $W_D$ has a duration of approximately 50-120 msec. A His bundle capture has occurred if an LVS event is detected within the window $W_D$, and that a para-Hisian capture has occurred if no LVS event is detected within the window $W_D$.

In some examples, the Hp-LV interval may be compared to an intrinsic His-to-left ventricular (Hs-LV) interval representing a time delay from an intrinsic His bundle activity (Hs) to the sensed LVS event. The intrinsic His bundle activity may be detected in response to an intrinsic sinus node firing during a sinus rhythm, or in response to an atrial pacing (AP) event. If the Hp-LV interval does not differ from the Hs-LV interval by more than a specified margin, then capture verification circuit 232 determines that a selective His bundle capture has occurred, which results fast conduction from the His bundle to the LV. However, if the Hp-LV interval exceeds the Hs-LV interval by more than the specified margin, then the conduction is deemed slow, and a non-selective His bundle capture or a para-Hisian capture is indicated.

In an example, the His-bundle capture status may be determined using a morphology of the LVS event detected from the sensed LV EGM. The LVS morphology may be determined from a uni-polar LV EGM that represents a more global perspective to the myocardial depolarization. A His-bundle capture is generally characterized by a narrower QRS complex due to fast conduction and more coordinated contraction of the left and right ventricles. A para-Hisian capture is generally characterized by wider QRS complex due to relatively slower muscle-to-muscle conduction, and less coordination between the left and right ventricles. A His-bundle capture is deemed to have occurred if the measured QRS width falls below a width threshold. A para-Hisian myocardial capture, absent of direct para-Hisian capture, is deemed to have occurred if the measured QRS interval exceeds the width threshold. In an example, the width threshold is approximately 90-120 msec. In another example, the width threshold is approximately 120-140 msec.

At 660, the His-bundle capture status may be assessed to determine whether a left-ventricular pacing is to be delivered. If no direct His-bundle capture is detected (with or without direct para-Hisian myocardial capture) at 660, then at 670 LV pacing (LVP) pulses may be generated, such as by the electrostimulation circuit 220, and delivered to one or more LV sites such as via one or more distal electrodes (e.g., the electrodes 132A-132C) associated with the lead 107. The LVP may be used as backup pacing to excite the myocardium and to prevent asystole following an unsuccessful HBP. In an example, the LVP may be delivered immediately following the end of a His-bundle capture detection window within which no direct His-bundle capture is detected. The LVP thus delivered is within the same cardiac cycle as the HBP. In another example, the LVP pulse may be delivered in a delayed fashion after a specific number of non-direct His-bundle capture beats. For example, backup LVP may be delivered if at least five non-direct His-bundle capture beats have been detected, or if at least five out of seven non-direct His-bundle capture beats have been detected.

The LVP may be delivered according to one or more parameters including parameters associated with amount of energy including, for example, pulse amplitude, pulse width, pulse frequency, pulse waveform, duty cycle, or stimulation duration. The LVP may be delivered using a uni-polar, a bi-polar, or an extended bipolar LVP pace vector. The LVP may be delivered in a single-site pacing (SSP) mode, or a multisite pacing (MSP) mode where two or more LV sites simultaneously or sequentially with a specified inter-site pacing delay, within the same cardiac cycle. In various examples, LV pace vector, pacing mode, or one or more pacing parameters may be selected or adjusted based on a level of normalization of the QRS duration (such as detected from the LV EGM) in response to HBP, or in response to integrated HBP and LVP delivered concurrently or sequentially. The LVP pulses may be delivered at specific time in a cardiac cycle according to one or more programmable timing parameters including, for example, an atrial-ventricular delay (AVD) representing a latency period from an AS event or an AP event to an LVP pulse, or an intra-ventricular pacing delay representing a time delay between pacing at multiple LV sites. In some examples, the LVP may include high-output pacing (HOP) pulses with higher stimulation energy than conventional pacing pulses. In some examples, the HOP pulses may be delivered on an intermittent basis, such that the conventional pacing pulses are delivered in 3-5 cardiac cycles between the HOP pulses.

If at 660 a His-bundle capture is indicated, then the process may continue at 620 to detect AS event and deliver triggered HBP. In some examples, the LVP pulses may be delivered concurrently with the delivery of the HBP pulse, or subsequent to the delivery of the HBP pulse after a specific time delay (not shown). In some patients, even a selective His-bundle capture at 660 may not adequately produce the same cardiac synchrony as would have happened with an intact His-Purkinje system. Concurrent or sequential pacing at the His bundle and at the left ventricle may help further improve the synchrony and cardiac performance in these patients.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for pacing a heart, comprising:
   an electrostimulation circuit configured to generate stimulation pulses for delivery at one or more target sites; and
   a control circuit configured to receive a cardiac activity, the control circuit including:
      a capture verification circuit configured to detect a His-bundle capture status using the received cardiac activity; and
      a pacing control circuit configured to control the electrostimulation circuit to:
         receive a programmed atrial-to-ventricular conduction delay distinct from an intrinsic atrial-to-His bundle interval;
         generate a His-bundle pacing (HBP) pulse and deliver the HBP pulse after a time interval shorter than the programmed atrial-to-ventricular conduction delay subsequent to an atrial activity to capture a His-bundle of the heart; and
         generate a left-ventricular pacing (LVP) pulse to capture a left ventricle of the heart if the detected His-bundle capture status, in response to the HBP pulse, satisfies a specific condition.

2. The system of claim 1, comprising an ambulatory medical device (AMD) that includes a sensing circuit configured to sense the cardiac activity, wherein the AMD is configured to be coupled to (1) a first lead associated with one or more electrodes to deliver the HBP pulse, and (2) a second lead associated with one or more left-ventricular electrodes to deliver the LVP pulse.

3. The system of claim 2, wherein the sensing circuit is configured to electrically couple to one or more atrial electrodes associated with the second lead to sense the atrial activity.

4. The system of claim 2, wherein:
   the sensing circuit is configured to be coupled to the one or more left-ventricular electrodes associated with the second lead to sense left ventricular activity of the heart in response to the delivery of the HBP pulse; and
   the capture verification circuit is configured to detect the His-bundle capture status using the sensed left ventricular activity.

5. The system of claim 4, wherein:
   the capture verification circuit is configured to detect the His-bundle capture status using a paced His-to-left ventricular (Hp-LV) interval representing a delay of the sensed left ventricular activity relative to the delivery of the HBP pulse; and
   the capture verification circuit is configured to detect the His-bundle capture status by comparing the Hp-LV interval to an intrinsic His-to-left ventricular (Hs-LV) interval measured during an intrinsic His-bundle activation.

6. The system of claim 4, wherein the capture verification circuit is configured to detect the His-bundle capture status based on a morphology of the sensed left ventricular activity.

7. The system of claim 1, wherein:
   the capture verification circuit is configured to detect the His-bundle capture status including to detect a presence or an absence of direct His-bundle depolarization resulted from the delivery of the HBP pulse; and the electrostimulation circuit is configured to generate the LVP pulse to capture the left ventricle in response to an absence of direct His-bundle depolarization.

8. The system of claim 7, wherein:
the capture verification circuit is further configured to classify the detected His-bundle capture status as one of a selective capture, a non-selective capture, a para-Hisian capture, or a loss of capture; and
the electrostimulation circuit is configured to generate the LVP pulse to capture the left ventricle if the detected His-bundle capture status is classified as a para-Hisian capture or a loss of capture.

9. The system of claim 7, wherein:
the pacing control circuit is configured to adjust one or more HBP parameters in response to the detection of an absence of direct His-bundle depolarization; and
the electrostimulation circuit is configured to generate an HBP pulse to capture the His- bundle according to the adjusted one or more HBP parameters.

10. The system of claim 9, wherein the electrostimulation circuit is configured to generate an HBP pulse to capture the His-bundle using an extended bipolar HBP vector in response to the detection of an absence of direct His-bundle depolarization, the extended bipolar HBP vector comprising a His-bundle electrode and a left-ventricular electrode.

11. The system of claim 10, wherein the pacing control circuit is configured to receive information about spatial proximity of each of two or more left-ventricular electrodes to a septum between ventricles of the heart, and to determine the extended bipolar HBP vector including to select the left-ventricular electrode from the two or more left-ventricular electrodes based on the received information about spatial proximity.

12. A system for pacing a heart, comprising:
an electrostimulation circuit configured to generate stimulation pulses for delivery at one or more target sites via at least first and second leads each including respective one or more electrodes;
a sensing circuit configured to sense a cardiac activity, including an atrial activity, via one or more electrodes included in the second lead; and
a control circuit configured to control the electrostimulation circuit to:
receive a programmed atrial-to-ventricular conduction delay distinct from an intrinsic atrial-to-His bundle interval;
generate a His-bundle pacing (HBP) pulse and deliver the HBP pulse via the first lead after a time interval shorter than the programmed atrial-to-ventricular conduction delay subsequent to the sensed atrial activity to capture a His-bundle of the heart; and
generate and deliver a left-ventricular pacing (LVP) pulse via the second lead to capture a left ventricle of the heart based on the sensed cardiac activity.

13. The system of claim 12, wherein the electrostimulation circuit is configured to deliver the HBP pulse and the LVP pulse concurrently with, or after a specific time delay subsequent to, the delivery of HBP pulse.

14. A method for pacing a heart using an ambulatory medical device electrically coupled to at least a first lead associated with one or more His-bundle electrodes and a second lead associated with one or more left-ventricular electrodes and one or more atrial electrodes, the method comprising:
receiving a programmed atrial-to-ventricular conduction delay distinct from an intrinsic atrial-to-His bundle interval;
generating a His-bundle pacing (HBP) pulse using an electrostimulation circuit and delivering the HBP pulse after a time interval shorter than the programmed atrial-to-ventricular conduction delay subsequent to an atrial activity to capture a His-bundle of the heart;
receiving a cardiac activity, in response to the delivered HBP pulses, via a sensing circuit and one or more electrodes associated with the first or second lead;
detecting a His-bundle capture status using the received cardiac activity; and
generate a left-ventricular pacing (LVP) pulse using the electrostimulation circuit and delivering the LVP pulse to capture a left ventricular site of the heart if the detected His-bundle capture status satisfies a specific condition.

15. The method of claim 14, wherein:
sensing the cardiac activity includes sensing left ventricular activity of the heart in response to the delivery of the HBP pulse using at least one of the one or more left-ventricular electrodes associated with the second lead to sense; and
detecting the His-bundle capture status includes using the sensed left ventricular activity.

16. The method of claim 15, wherein:
sensing the left ventricular activity includes a paced His-to-left ventricular (Hp-LV) interval representing a delay of the sensed left ventricular activity relative to the delivery of the HBP pulse; and
detecting the His-bundle capture status using a comparison of the Hp-LV interval to an intrinsic His-to-left ventricular (Hs-LV) interval measured during an intrinsic His-bundle activation.

17. The method of claim 15, wherein:
detecting the His-bundle capture status includes detecting a presence or an absence of direct His-bundle depolarization resulted from the delivery of the HBP pulse; and
generating the LVP pulse to capture the left ventricle is in response to the detection of an absence of direct His-bundle depolarization.

18. The method of claim 17, further comprising:
adjusting one or more HBP parameters in response to the detection of an absence of direct His-bundle depolarization; and
generating an HBP pulse to capture the His-bundle according to the adjusted one or more HBP parameters.

19. The method of claim 18, wherein adjusting the one or more HBP parameters includes switching to an extended bipolar HBP vector in response to the detection of an absence of direct His-bundle depolarization, the extended bipolar HBP vector comprising a His-bundle electrode and a left-ventricular electrode.

20. The method of claim 14, comprising delivering the LVP pulse concurrently with, or after a specific time delay subsequent to, the delivery of HBP pulse.

* * * * *